United States Patent
Korte et al.

(10) Patent No.: US 11,238,960 B2
(45) Date of Patent: Feb. 1, 2022

(54) DETERMINING JOURNALIST RISK OF A DATASET USING POPULATION EQUIVALENCE CLASS DISTRIBUTION ESTIMATION

(71) Applicant: Privacy Analytics Inc., Ottawa (CA)

(72) Inventors: Stephen Korte, Ottawa (CA); Luk Arbuckle, Ottawa (CA); Andrew Baker, Alcove (CA); Khaled El Emam, Ottawa (CA); Sean Rose, Ottawa (CA)

(73) Assignee: Privacy Analytics Inc., Ottawa (CA)

( * ) Notice: Subject to any disclaimer, the term of this patent is extended or adjusted under 35 U.S.C. 154(b) by 895 days.

(21) Appl. No.: 14/953,195

(22) Filed: Nov. 27, 2015

(65) Prior Publication Data
US 2016/0155061 A1 Jun. 2, 2016

Related U.S. Application Data

(60) Provisional application No. 62/085,307, filed on Nov. 27, 2014.

(51) Int. Cl.
*G16H 10/60* (2018.01)

(52) U.S. Cl.
CPC .................. *G16H 10/60* (2018.01)

(58) Field of Classification Search
CPC ...................................... G16H 10/60
USPC ........................................................ 706/52
See application file for complete search history.

(56) References Cited

U.S. PATENT DOCUMENTS

2007/0026365 A1* 2/2007 Friedrich ................. G16B 5/00
434/127
2010/0077006 A1* 3/2010 El Emam .......... G06F 17/30536
707/785

FOREIGN PATENT DOCUMENTS

CA 2734545 A1 * 9/2011 ........... G06F 21/577

OTHER PUBLICATIONS

Danker et al., "A Method for Evaluating Marketer Re-Identification Risk", PAIS'10, Mar. 22-26, 2010 (Year: 2010).*
Emam, et al., "Protecting Privacy Using k-Anonumity", Journal of the American Medical Informatics Association, vol. 15, No. 5, Sep./Oct. 2008 (Year: 2008).*
Ferrari, et al., "Smooth Function Approximation Using Neural Networks", IEEE Transactions on Neural Network, vol. 16, No. 1, Jan. 2005 (Year: 2005).*
El Emam, et al., "Evaluating the Risk of Re-identification of Patients from Hospital Prescription Records", Can J. Hosp Pharm 2009;62(4):307-319 (Year: 2009).*
Vapnik, et al., "An Overview of Statistical Learning Theory", IEEE Transactions on Neural Networks, vol. 10, No. 5, Sep. 1999 (Year: 1999).*

* cited by examiner

*Primary Examiner* — Tsu-Chang Lee
(74) *Attorney, Agent, or Firm* — John Maldjian; Patrick Garrett; Stevens & Lee PC

(57) ABSTRACT

A system, method and computer readable memory for determining journalist risk of a dataset using population equivalence class distribution estimation. The dataset may be a cross-sectional data set or a longitudinal dataset. The determine risk of identification can be determined and used in de-identification process of the dataset.

21 Claims, 3 Drawing Sheets

US 11,238,960 B2

DETERMINING JOURNALIST RISK OF A DATASET USING POPULATION EQUIVALENCE CLASS DISTRIBUTION ESTIMATION

CROSS REFERENCE

This application claims priority from United States Provisional Application No. 62/085,307 filed Nov. 27, 2014 the entirety of which is incorporated by reference for all purposes.

TECHNICAL FIELD

The present disclosure relates to databases and particularly to protecting privacy by estimating risk of identification of personal data stored in the databases.

BACKGROUND

Personal information is being continuously captured in a multitude of electronic databases. Details about health, financial status and buying habits are stored in databases managed by public and private sector organizations. These databases contain information about millions of people, which can provide valuable research, epidemiologic and business insight. For example, examining a drugstore chain's prescriptions can indicate where a flu outbreak is occurring. To extract or maximize the value contained in these databases, data custodians must often provide outside organizations access to their data. In order to protect the privacy of the people whose data is being analyzed, a data custodian will "de-identify" or "anonymize" information before releasing it to a third-party. An important type of de-identification ensures that data cannot be traced to the person about whom it pertains, this protects against 'identity disclosure'.

When de-identifying records, many people assume that removing names and addresses (direct identifiers) is sufficient to protect the privacy of the persons whose data is being released. The problem of de-identification involves those personal details that are not obviously identifying. These personal details, known as quasi-identifiers, include the person's age, sex, postal code, profession, ethnic origin and income, financial transactions, medical procedures (to name a few). To be able to de-identify data the assessment of the risk of re-identification is required to be determined. Therefore there is a need for improved risk assessment of data sets.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
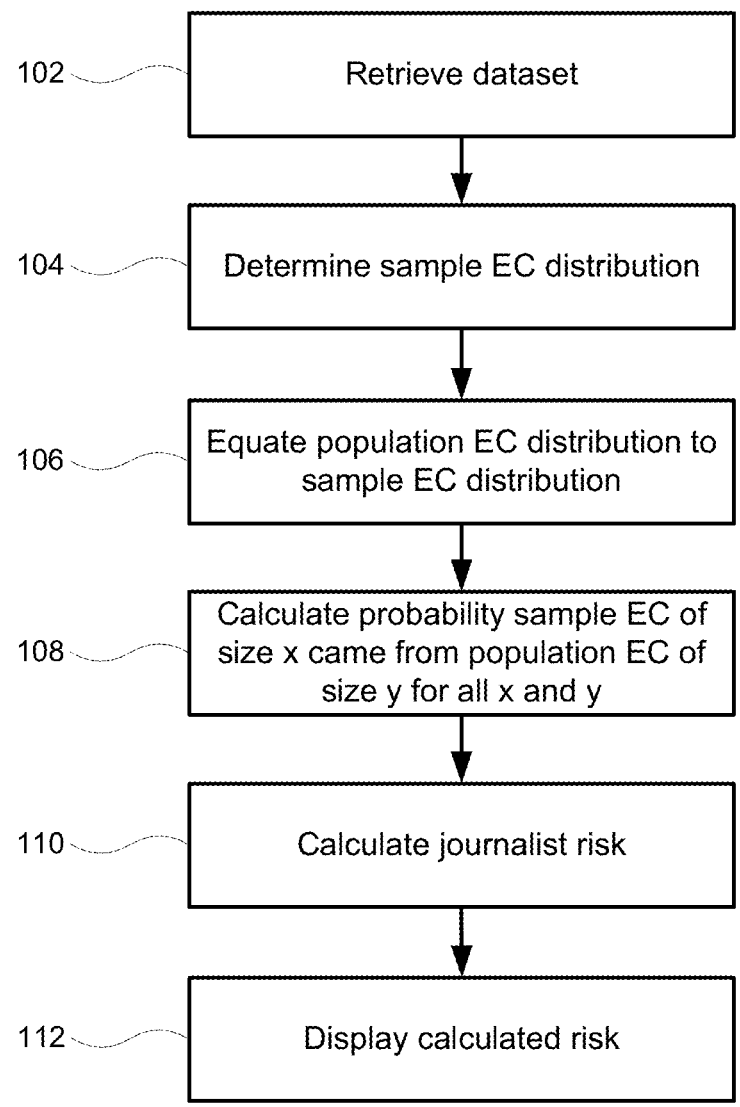
FIG. 1 shows a method for determining journalist risk for a cross-sectional dataset using population equivalence class distribution estimation.

In accordance with an aspect of the present disclosure there is provided a computer implemented method of determining journalist risk associated with a dataset, the method comprising: retrieving the dataset containing a plurality of records containing personal data, the dataset representing a sample of individuals and data associated with a larger population; determining sample equivalence class (EC) distribution of the dataset; equating a population EC distribution to the determined sample EC distribution; calculating probability that an EC in the dataset of size x came from population of size y for all x and y; and calculating the journalist risk measurement using calculated probability; wherein the equivalence classes define a collection of all records in the dataset containing identical values for all quasi-identifiers in the data.

In accordance with another aspect of the present disclosure there is provided a system for determining journalist risk associated with a dataset, the system comprising: a memory containing the dataset containing a plurality of records containing personal data, the dataset representing a sample of individuals and data associated with a larger population, dataset having equivalence classes defining a collection of all records in the dataset containing identical values for all quasi-identifiers in the data; and a processor coupled to the memory, the processor executing instructions for: determining sample equivalence class (EC) distribution of the dataset; equating a population EC distribution to the determined sample EC distribution; calculating probability that an EC in the dataset of size x came from population of size y for all x and y; and calculating the journalist risk measurement using calculated probability.

In accordance with yet another aspect of the present disclosure there is provided a non-transitory computer readable memory containing instructions for determining journalist risk associated with a dataset, the instructions which when executed by a processor perform: retrieve the dataset containing a plurality of records containing personal data, the dataset representing a sample of individuals and data associated with a larger population; determine sample equivalence class (EC) distribution of the dataset; equate a population EC distribution to the determined sample EC distribution; calculate probability that an EC in the dataset of size x came from population of size y for all x and y; and calculate the journalist risk measurement using calculated probability; wherein the equivalence classes define a collection of all records in the dataset containing identical values for all quasi-identifiers in the data.

Embodiments are described below, by way of example only, with reference to FIGS. 1-3.

The methodology presented can augment the risk measurement processes within risk measurement and de-identification software. It handles the case when the dataset on which risk is being measured, is a sample of a larger dataset; these will be referred to as the sample and the population, respectively. It is further assumed that the dataset is a random sample of the population or that it is sampled on some unknowable attribute. For example, measuring journalist risk would not be appropriate in the case of a sample dataset of all births of twins from a birth database. A dataset is longitudinal if it tracks the same type of information on the same subjects at multiple points in time. For example, part of a longitudinal dataset could contain specific patients and their medical results over a period of years. Each patient may have varying times and number of visits. A cross-sectional dataset comprises data collected on many subjects at the same point of time, or without regard to differences in time. Analysis of cross-sectional datasets usually consists of comparing the differences among the subjects.

In the description the following terms are used:
Equivalence Class: collection of all individuals in a dataset containing identical values for all quasi-identifiers.
Similarity Measure: used in the context of longitudinal risk measurement, it is the number of individuals who look like a given individual in a dataset.
Journalist Risk: Risk measured when the dataset is a sample of a larger dataset.
Prosecutor Risk: Risk measured only in reference to the dataset itself.

Average Risk Measurement:

The method by which average risk can be measured for both cross-sectional and longitudinal data can be equivalent to calculating the risk of re-identification of every patient in the database and then taking the average.

The re-identification risk of a record is 1/F where F is either the similarity measure of the record (for longitudinal data) or the size of the equivalence class the record belongs to (for cross-sectional data). Because it is possible to construct an alias equivalence class distribution from the similarity measure distribution, risk can measured once the appropriate equivalence class distribution is known.

When prosecutor risk is being measured and the dataset does not represent a sample, the equivalence class distribution of the dataset is used to measure the risk However, when the dataset represents a sample, F would be the size of the equivalence class to which the patient belongs in the population. Generally, it is not possible to know the equivalence class distribution of the population or the population equivalence class size from which the record was sampled.

Maximum Risk Measurement

Maximum journalist risk can be found by inverting the minimum similarity measure in the population for longitudinal data or inverting the minimum equivalence class size in the population for cross-sectional data.

Cross-Sectional Dataset

To begin, the estimation of the population equivalence class distribution and the subsequent risk measurement will be considered within the context of a cross-sectional dataset. Referring to FIG. 1, journalist risk for cross-sectional dataset using population equivalence class distribution estimation can be assessed by retrieving the data set from a store (102). The dataset may be accessed in whole or in segments either stored local or remotely by a computing device.

Estimating Population Equivalence Class Distribution

The sample equivalence class (EC) distribution is determined from dataset (104). In order measure journalist risk for cross-sectional data, the population equivalence class distribution must be estimated. Following a method developed by Zayatz, L. (Estimation of the percent of unique population elements on a microdata file using the sample. Washington: US Bureau of the Census; 1991) the initial assumption that the population equivalence class distribution can be equated to the sample equivalence class distribution is made (106).

From there a combinatorics calculation gives the probability that an equivalence class of size x in the sample came from an equivalence class of size y in the population. First, the probability that an equivalence class of size y in the population will be sampled to an equivalence class of size x in the sample, is calculated:

$$Pr(\text{size } x \text{ in sample} | \text{size } y \text{ in population}) = \binom{y}{x}\binom{N-y}{n-x} / \binom{N}{n}$$

where n is the sample size, N is the population size and $$\binom{y}{x} = \frac{y!}{x!(y-x)!}$$

The probability that an equivalence class is of size y in the population and is an equivalence class of size x in the population will be:

$$Pr(\text{size } x \text{ in sample} | \text{size } y \text{ in population}) \times Pr(y)$$

where Pr(y)=num. of equivalence classes of size y in pop./total number of equivalence classes in population. Because of the assumption that the equivalence class distributions of the sample and population are the same, it may also be written that:

$Pr(y)$=num. of equivalence classes of size $y$ in sample/total number of equivalence classes in sample Finally Bayes' theorem can be applied in conjunction with the law of total probability to calculate the probability that an equivalence class of size x in the sample came from an equivalence class of size y in the population:

$$Pr(\text{size } y \text{ in population} | \text{size } x \text{ in sample}) = \frac{Pr(y) \times Pr(\text{size } x \text{ in sample} | \text{size } y \text{ in population})}{\sum_{c=x}^{max\ size} Pr(C) \times Pr(\text{size } x \text{ in sample} | \text{size } C \text{ in population})}$$

where max size is the maximum equivalence class size in the sample and the population. The probability sample EC of size x came from population EC of size y for all x and y is then calculated (108). These probabilities will be used to calculate journalist risk (112) as described below.

Calculating Journalist Risk

Without any consideration of a population, the average prosecutor risk may be calculated by dividing the proportion of records belong to equivalence classes of a given size, by the equivalence class size and summing the result:

$$Risk_{prosecutor} = \sum_{i=1}^{max\ size} Prop(i)/i$$

where Prop(i)=number of records in equivalence classes of size i/n

This equation is modified to calculate journalist risk when the dataset is recognized as a sample:

$$Risk_{journalist} = \sum_{i=1}^{max\ size} \sum_{j=i}^{max\ size} Pr(\text{size } j \text{ in } pop. | \text{size } i \text{ in } samp.) \times Prop(i)/j$$

This journalist risk equation assumes the re-identification attack involves choosing someone from the sample and trying to re-identify them in the population. An alternate attack would see an adversary trying to match someone from the population in the sample. The risk in that case would be:

$$Risk_{journalist} = J \Big/ \sum_{i=1}^{max\ size} \sum_{j=i}^{max\ size} Pr(\text{size } j \text{ in } pop. | \text{size } i \text{ in } samp.) \times EC\_num(i) \times j$$

where J is the number of equivalence classes in the sample and EC_num(i) is the number of equivalence classes of size i in the sample.

Overall, journalist risk will be the maximum of these two risk calculations.

Longitudinal Dataset

Calculating journalist risk for longitudinal data will incorporate the methodology involved in calculating journalist risk for cross-sectional data as described in connection with FIG. 1. With reference to FIG. 2, when dealing with a longitudinal dataset, instead of grouping records into equivalence classes, a similarity measure is calculated for each individual in the dataset. The similarity measure is a description of how many other individuals that individual looks like. The dataset may be retrieved or accessed in whole or in segments either stored local or remotely by a computing device (202).

Similarity measures for the dataset are determined (204). The reason that equivalence classes are not formed is because the measure for defining what it means for a selected individual to be similar to another individual is non-commutative: patient A might be similar to patient B, but patient B might not be similar to patient A. As an example, consider two individuals with the same values for all demographic quasi-identifiers. Patient A has disease X, while patient B has disease X and Y. An adversary trying to re-identify Patient A will look for patients with disease X and will find two such patients: patient B is similar to patient A. An adversary trying to re-identify Patient B will look for patients with disease X and Y and will only find one such patient: in this case patient A is not similar to patient B.

An equivalence class distribution is required for the Zayatz method and so the similar measure distribution must be transformed. A consequence of the non-commutative nature of the similarity measure is that the corresponding equivalence class distribution might contain non-integer values.

For example it might be determined that there are 3 individuals with similarity measures of 4, in which case the number of equivalence classes of size 4 would be ¾=0.75.

There are no difficulties in using non-integer equivalence counts with the population equivalence class estimation methodology as it only uses the corresponding probability distribution created by dividing the equivalence class size counts by the total number of equivalence classes.

Before the similarity measure distribution is converted to an equivalence class distribution, the similarity measure for each individual in the data set must be rounded to an integer value (206). The reason it may not be an integer value, is because when determining how many individuals a particular individual looks like, multiple combinations of the patients' records will be considered individually yielding multiple integers which must then be averaged.

A rounding step is necessary for two reasons. Firstly, the similarity measure directly translates into an equivalence class size in the process described above. A combinatoric approach is used where integer sizes are implicitly assumed. Secondly, the method considers individuals who have the same number of individuals who are similar to them as equivalence classes. So if there are individuals with similarity counts of 2.90, 3, 3.1, it is desirable to model them as one equivalence class of size 3. This would not be the case unless rounding is performed. The number of each similarity measure count is divided by the measure to obtain sample EC distribution (208).

Once the similarity measure distribution of a longitudinal data set is converted to an equivalence class distribution (210), the same risk measurement steps are followed that have been previously detailed for a cross-sectional data set in reference to FIG. 1.

Measuring Longitudinal Risk by Taking Sample

There may be datasets that are so large that it becomes impractical to determine a similarity count for every individual in a longitudinal dataset. The similarity counts for a certain percentage of individuals in the sample dataset can be determined and subsequently the similarity counts for the entire dataset could be estimated by dividing those similarity counts by the percentage of individuals used to construct the counts.

For example if 10% of individuals in a dataset had their similarity measures determined and aggregated into counts by comparing against all individuals in the dataset, the similarity counts for the dataset would be determined by dividing those counts by 0.10. These counts would represent an estimate for the similarity measure counts in the sample dataset. The probability sample EC of size x came from population EC of size y for all x and y is then calculated (212). These numbers would then be used to begin the process for measuring journalist risk (214) as discussed above. The calculated risk for the dataset can then be presented (216), and as described above.

Figure 3:
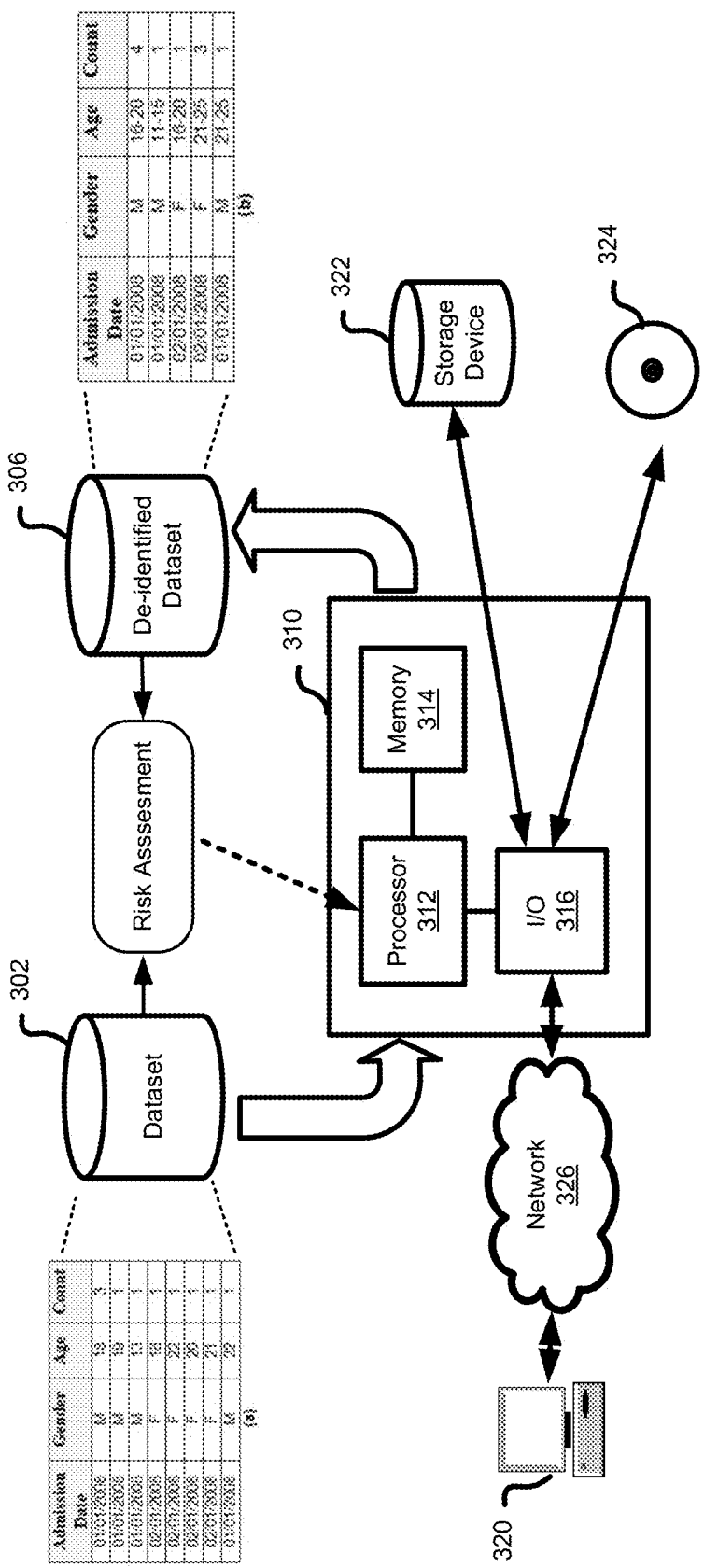
FIG. 3 shows system for determining journalist risk of a dataset using population equivalence class distribution estimation.

FIG. 3 provides a system for journalist risk assessment using population equivalence class distribution estimation as used in connection with the above described method. A computer or server 310 providing at least a processor 312, memory 314 and input/output interface 316, implements the code for executing the de-identification process. A source dataset 302 is stored on non-transitory computer readable storage memory which may reside locally or remotely from processing unit 312. The dataset is processed by the computer 310 to provide risk assessment which can be used for the optimal de-identification. Generalization strategies and levels of suppression can also be provided through template files, user selection or input through interaction with the computer 310, either directly through input devices such a keyboard/mouse and display or remotely through a connected computing network 326. External storage 322, or computer readable memory such as compact disc, digital versatile disc or other removable memory devices 324 may be used to provide the instructions for execution of the risk assessment and de-identification methods or provide input for generalization or suppression parameters via I/O unit 316. Execution of the method on processor 312 retrieves 306 and provides an assessment of risk or provide the resulting parameters which can be utilized in performing de-identification of the dataset to meet a desired risk threshold. The de-identification process may use optimization such as optimal lattice anonymization for determine a level of de-identification which meets desired risk threshold.

Each element in the embodiments of the present disclosure may be implemented as hardware, software/program, or any combination thereof. Software codes, either in its entirety or a part thereof, may be stored in a non-transitory computer readable medium or memory (e.g., as a RAM, ROM, for example a non-volatile memory such as flash memory, CD ROM, DVD ROM, Blu-ray™, a semiconductor ROM, USB, or a magnetic recording medium, for example a hard disk). The program may be in the form of source code, object code, a code intermediate source and object code such as partially compiled form, or in any other form.

Figure 2:
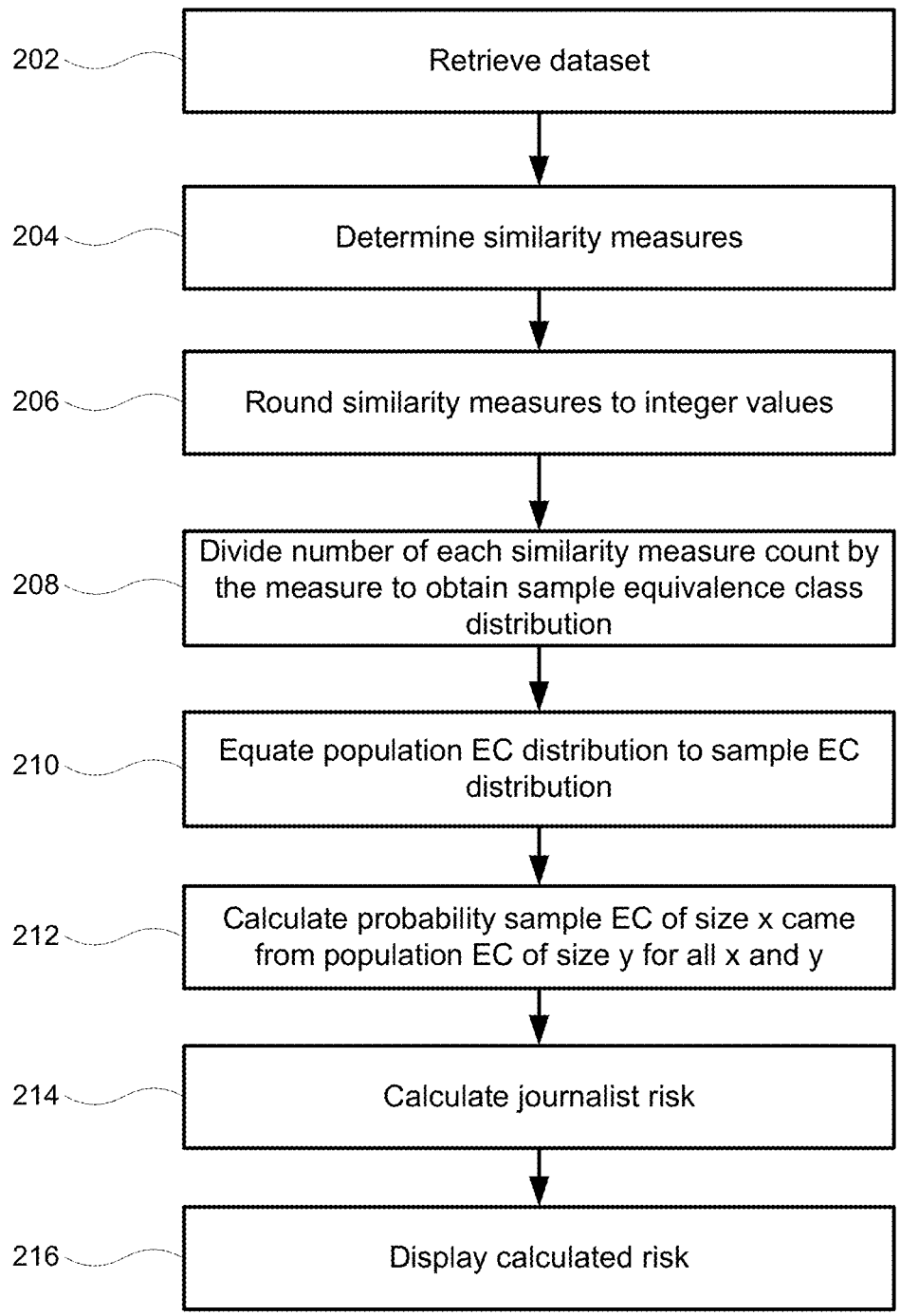
FIG. 2 shows a method for determining journalist risk for a longitudinal dataset using population equivalence class distribution estimation.

It would be appreciated by one of ordinary skill in the art that the system and components shown in FIGS. 1-3 may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims.

The invention claimed is:

1. A method of determining a journalist risk associated with a longitudinal dataset having personal data, including quasi-identifiers, of individuals representing a sample of a population in a database, the method comprising, on a computing device:
   determining, from cross-sectional data in the longitudinal dataset for each of the individuals represented in the sample, a similarity measure;
   rounding the similarity measure to an integer value, wherein using a combinatorics approach, the integer value of the rounded similarity measure directly translates to a respective one of equivalence classes, each including a subset of the individuals having identical values for all the quasi-identifiers, each subset having a subset size; and
   for each of the equivalence classes:
      obtaining a sample equivalence class distribution by dividing the rounded similarity measure by the determined similarity measure, wherein the obtained sample equivalence class distribution is a population equivalence class distribution;
      calculating a probability that the equivalence class of a first size comes from population of the equivalence class of a second size;
      calculating an average prosecutor risk, without consideration of the population, by dividing a proportion of the individuals that belong to the equivalence class by the subset size of the equivalence class and summing the result;
      determining the journalist risk by multiplying the proportion of the individuals that belong to the equivalence class by the calculated probability;
      de-identifying the database based on the journalist risk to provide a de-identified database; and
      displaying the journalistic risk on a display of the computing device.

2. The method of claim 1, wherein the calculating the probability that the equivalence class of the first size y in the population will be sampled to an equivalence class of the second size x in the sample, comprises computing:

$$Pr(\text{size } x \text{ in sample} | \text{size } y \text{ in population}) = \binom{y}{x}\binom{N-y}{n-x} / \binom{N}{n}$$

where n is a sample size, N is a population size and $$\binom{y}{x} = \frac{y!}{x!(y-x)!}.$$

3. The method of claim 2, wherein the probability that the equivalence class is of the subset size y in the population and is the equivalence class of the subset size x in the population is:

$$Pr(\text{size } x \text{ in sample} | \text{size } y \text{ in population}) \times Pr(y)$$

where Pr(y)=a number of the equivalence classes of the subset size y in population/a total number of the equivalence classes in the population.

4. The method of claim 3, wherein the determining the journalist risk comprises computing:

$$Risk_{journalist} = \sum_{i=1}^{max\_size} \sum_{j=i}^{max\_size} Pr(\text{size } j \text{ in } pop. | \text{size } i \text{ in } samp.) \times Prop(i)/j$$

where Prop(i)=number of individuals in the equivalence classes of the subset size i/n.

5. The method of claim 1, wherein the determining the journalist risk comprises:
   matching personal data of someone from the population in the sample; and
   computing $$Risk_{journalist} = J \bigg/ \sum_{i=1}^{max\_size} \sum_{j=i}^{max\_size} Pr(\text{size } j \text{ in } pop. | \text{size } i \text{ in } samp.) \times EC\_num(i) \times j$$

where J is the number of equivalence classes in the sample and EC_num(i) is the number of equivalence classes of the subset size i in the sample.

6. A system to determine a journalist risk associated with a longitudinal dataset having personal data, including quasi-identifiers, of individuals representing a sample of a population in a database, the system comprising a processor configured to:
   determine, from cross-sectional data in the longitudinal dataset for each of the individuals represented in the sample, a similarity measure;
   round the similarity measure to an integer value, wherein using a combinatorics approach, the integer value of the rounded similarity measure directly translates into a respective one of equivalence classes, each including a subset of the individuals having identical values for all the quasi-identifiers, each subset having a subset size; and
   for each of the equivalence classes:
      obtain a sample equivalence class distribution by dividing the rounded similarity measure by the determined similarity measure, wherein the obtained sample equivalence class distribution is a population equivalence class distribution;
      calculate a probability that the equivalence class of a first size comes from population of the equivalence class of a second size;

calculate an average prosecutor risk, without consideration of the population, by dividing a proportion of the individuals that belong to the equivalence class by the subset size of the equivalence class and summing the result;

determine the journalist risk by multiplying the proportion of records that belong to the equivalence class by the calculated probability;

de-identify the database based on the journalist risk to provide a de-identified database; and displaying the journalistic risk on a display associated with the processor.

7. The system of claim 6, wherein the processor is further configured to:

calculate the probability that an equivalence class of the subset size y in the population is sampled to an equivalence class of the subset size x in the sample, using:

$$Pr(\text{size } x \text{ in sample} | \text{size } y \text{ in population}) = \binom{y}{x}\binom{N-y}{n-x} / \binom{N}{n}$$

where n is the sample size, N is the population size and $$\binom{y}{x} = \frac{y!}{x!(y-x)!}.$$

8. The system of claim 7, wherein the probability that the equivalence class is of the subset size y in the population and is the equivalence class of the subset size x in the population is:

$$Pr(\text{size } x \text{ in sample} | \text{size } y \text{ in population}) \times Pr(y)$$

where Pr(y)=a number of the equivalence classes of the subset size y in population/a total number of the equivalence classes in the population.

9. The system of claim 8, wherein the journalist risk is determined by:

$$Risk_{journalist} = \sum_{i=1}^{max\_size} \sum_{j=i}^{max\_size} Pr(\text{size } j \text{ in } pop. | \text{size } i \text{ in } samp.) \times Prop(i)/j$$

where Prop(i)=number of individuals in the equivalence classes of the subset size i/n.

10. The system of claim 6, wherein the journalist risk is based upon matching personal data of someone from the population in the sample, and the processor is further configured a formula of:

$$Risk_{journalist} =$$
$$J \Big/ \sum_{i=1}^{max\_size} \sum_{j=i}^{max\_size} Pr(\text{size } j \text{ in } pop. | \text{size } i \text{ in } samp.) \times EC\_num(i) \times j$$

where J is the number of equivalence classes in the sample and EC_num(i) is the number of equivalence classes of the subset size i in the sample.

11. A non-transitory computer readable medium encoded with a computer program to determine a journalist risk associated with a longitudinal dataset having personal data, including quasi-identifiers, of individuals representing a sample of a population in a database, wherein the computer program comprises instructions to cause a processor to:

determine, from cross-sectional data in the longitudinal dataset for each of the individuals represented in the sample, a similarity measure;

round the similarity measure to an integer value, wherein using a combinatorics approach, the integer value of the rounded similarity measure directly translates into a respective one of equivalence classes, each including a subset of the individuals having identical values for all the quasi-identifiers, each subset having a subset size; and for each of the equivalence classes:

obtain a sample equivalence class distribution by dividing the rounded similarity measure by the determined similarity measure, wherein the obtained sample equivalence class distribution is a population equivalence class distribution;

calculate a probability that the equivalence class of a first size comes from population of the equivalence class of a second size;

calculate an average prosecutor risk, without consideration of the population, by dividing a proportion of the individuals that belong to the equivalence class by the subset size of the equivalence class and summing the result;

determine the journalist risk by multiplying the proportion of records that belong to the equivalence class by the calculated probability;

de-identify the database based on the journalist risk to provide a de-identified database; and display the journalistic risk on a display associated with the processor.

12. The non-transitory computer readable medium of claim 11, further comprising instructions to cause the processor to:

calculate the probability that an equivalence class of the subset size y in the population is sampled to an equivalence class of the subset size x in the sample, using:

$$Pr(\text{size } x \text{ in sample} | \text{size } y \text{ in population}) = \binom{y}{x}\binom{N-y}{n-x} / \binom{N}{n}$$

where n is the sample size, N is the population size and $$\binom{y}{x} = \frac{y!}{x!(y-x)!}.$$

13. The non-transitory computer readable medium of claim 12, wherein the probability that the equivalence class is of the subset size y in the population and is the equivalence class of the subset size x in the population is:

$$Pr(\text{size } x \text{ in sample} | \text{size } y \text{ in population}) \times Pr(y)$$

where Pr(y)=a number of the equivalence classes of the subset size y in population/a total number of the equivalence classes in the population.

14. The non-transitory computer readable medium of claim 13, further comprising instructions to cause the processor to determine the journalist risk as:

$$Risk_{journalist} = \sum_{i=1}^{max\_size} \sum_{j=i}^{max\_size} Pr(\text{size } j \text{ in } pop. | \text{size } i \text{ in } samp.) \times Prop(i)/j$$

where Prop(i)=number of individuals in the equivalence classes of the subset size i/n.

15. The non-transitory computer readable medium of claim 11, wherein the journalist risk is based upon matching personal data of someone from the population in the sample, and the processor is further configured a formula of:

$$Risk_{journalist} = J \Bigg/ \sum_{i=1}^{max\_size} \sum_{j=i}^{max\_size} Pr(\text{size } j \text{ in } pop. | \text{size } i \text{ in } samp.) \times EC\_num(i) \times j$$

where J is the number of equivalence classes in the sample and EC_num(i) is the number of equivalence classes of the subset size i in the sample.

16. The non-transitory computer readable medium of claim 11, further including instructions to cause the processor to:

determine the journalistic risk based on optimal lattice anonymization.

17. The method of claim 1, wherein the determining the journalistic risk comprises:

determining the journalistic risk based on optimal lattice anonymization.

18. The method of claim 6, wherein the processor is further configured to:

determine the journalistic risk based on optimal lattice anonymization.

19. The method of claim 1, wherein the database contains records of millions of people, and wherein the de-identifying comprises:

de-identifying the database containing records of millions of people based on the journalist risk to provide the de-identified database.

20. The system of claim 6, wherein the database contains records of millions of people, and wherein the processor is further configured to:

de-identify the database containing records of millions of people based on the journalist risk to provide the de-identified database.

21. The non-transitory computer readable medium of claim 11, wherein the database contains records of millions of people, further comprising instructions to cause the processor to:

de-identify the database containing records of millions of people based on the journalist risk to provide the de-identified database.

* * * * *

UNITED STATES PATENT AND TRADEMARK OFFICE
CERTIFICATE OF CORRECTION

PATENT NO. : 11,238,960 B2
APPLICATION NO. : 14/953195
DATED : February 1, 2022
INVENTOR(S) : Korte et al.

It is certified that error appears in the above-identified patent and that said Letters Patent is hereby corrected as shown below:

On the Title Page

Item (56), Column 2, under "References Cited – OTHER PUBLICATIONS", Line 3, after "Using", replace "k-Anonumity" with "k-Anonymity".

Signed and Sealed this
Seventeenth Day of May, 2022

Katherine Kelly Vidal
*Director of the United States Patent and Trademark Office*